US00PP31955P3

(12) United States Plant Patent
Hock

(10) Patent No.: US PP31,955 P3
(45) Date of Patent: Jul. 7, 2020

(54) ***DRACAENA* PLANT NAMED 'CANTIK'**

(50) Latin Name: *Dracaena surculosa*
Varietal Denomination: CANTIK

(71) Applicant: Nieuwkoop Europe BV, De Kwakel (NL)

(72) Inventor: Lee Chee Hock, Kota Tinggi (MY)

(73) Assignee: Nieuwkoop Europe B.V., De Kwakel (NL)

( * ) Notice: Subject to any disclaimer, the term of this patent is extended or adjusted under 35 U.S.C. 154(b) by 0 days.

(21) Appl. No.: 16/602,318

(22) Filed: Sep. 12, 2019

(65) Prior Publication Data

US 2020/0093049 P1 Mar. 19, 2020

(30) Foreign Application Priority Data

Sep. 13, 2018 (QZ) ..... PBR 2018/2354

(51) Int. Cl.
*A01H 5/00* (2018.01)
*A01H 6/12* (2018.01)

(52) U.S. Cl.
USPC ..... Plt./383
CPC ..... *A01H 6/12* (2018.05)

(58) Field of Classification Search
USPC ..... Plt./383
CPC ..... A01H 5/00; A01H 6/12
See application file for complete search history.

*Primary Examiner* — Annette H Para
(74) *Attorney, Agent, or Firm* — Samuel R. McCoy, Jr.

(57) ABSTRACT

A new and distinct *Dracaena surculosa* plant named 'CANTIK' which is characterized by the combination of a freely branching, upright growth habit with an abundance of foliage born on strong upright stems, dark green and glossy foliage which is sparsely to moderately and irregularly dotted yellow-green with aging foliage that is blushed and marbled with a lighter shade of green, and the stability of these characteristics from generation to generation.

2 Drawing Sheets

Latin name of the genus and species: The Latin name of the genus and species of the novel variety disclosed herein is *Dracaena surculosa.*

Variety denomination: The inventive cultivar of *Dracaena* disclosed herein has been given the variety denomination 'CANTIK'.

BACKGROUND OF THE INVENTION

Parentage: 'CANTIK' is a spontaneous whole-plant mutation of an unnamed *Dracaena surculosa* plant (not patented) which was discovered in Kota Tinggi, Johor, Malaysia in the spring of 2016. The mutation was initially noted for its large, dark green foliage. Said mutation was isolated for further evaluation to confirm the uniformity and stability of the unique characteristics first observed. Upon confirmation of the stability and uniformity of the characteristics, the new plant was selected for commercialization.

Asexual Reproduction: Asexual reproduction of 'CANTIK', by way of softwood stem cuttings, was first performed in the spring of 2016 in Kota Tinggi, Johor, Malaysia. Through five subsequent generations, the unique features of this cultivar have proven to be stable and true to type.

SUMMARY OF THE INVENTION

The cultivar 'CANTIK' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'CANTIK'. These characteristics in combination distinguish 'CANTIK' as a new and distinct *Dracaena surculosa* cultivar:

1. *Dracaena* 'CANTIK' exhibits a freely branching, upright growth habit with an abundance of foliage born on strong, upright stems; and
2. *Dracaena* 'CANTIK' exhibits dark green, glossy foliage which is sparsely to moderately and irregularly dotted yellow-green; and
3. *Dracaena* 'CANTIK' exhibits aging foliage which is blushed and marbled with a lighter shade of green.

BOTANICAL DESCRIPTION OF THE PLANT

Figure 1:
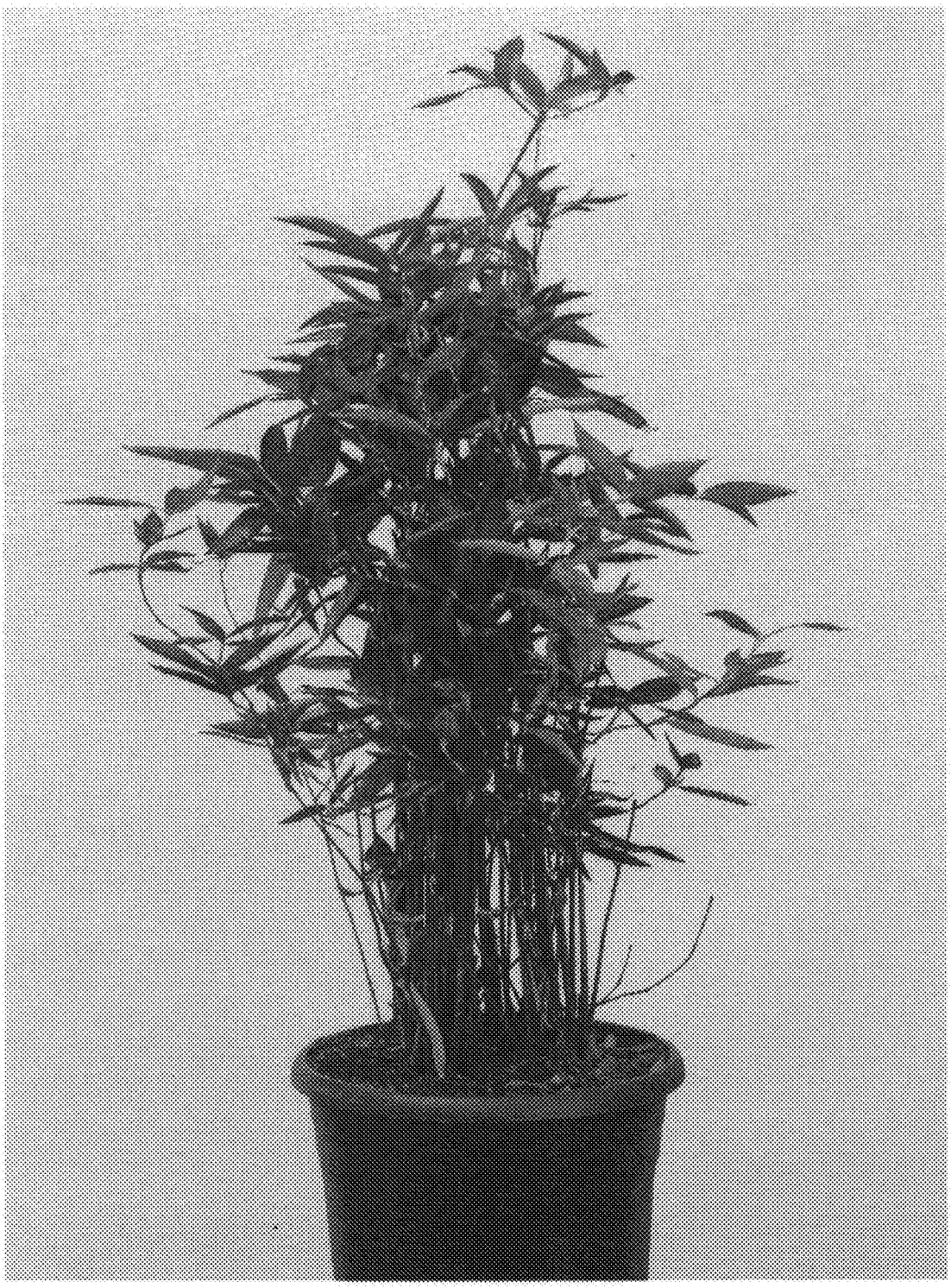
FIG. 1 illustrates, as nearly true as it is reasonably possible to make the same in color photographs of this type, an exemplary plant of 'CANTIK' grown in Kota Tinggi, Johor, Malaysia. This plant, grown in a 23 cm nursery container, is approximately two years old from a rooted young plant.
Figure 2:
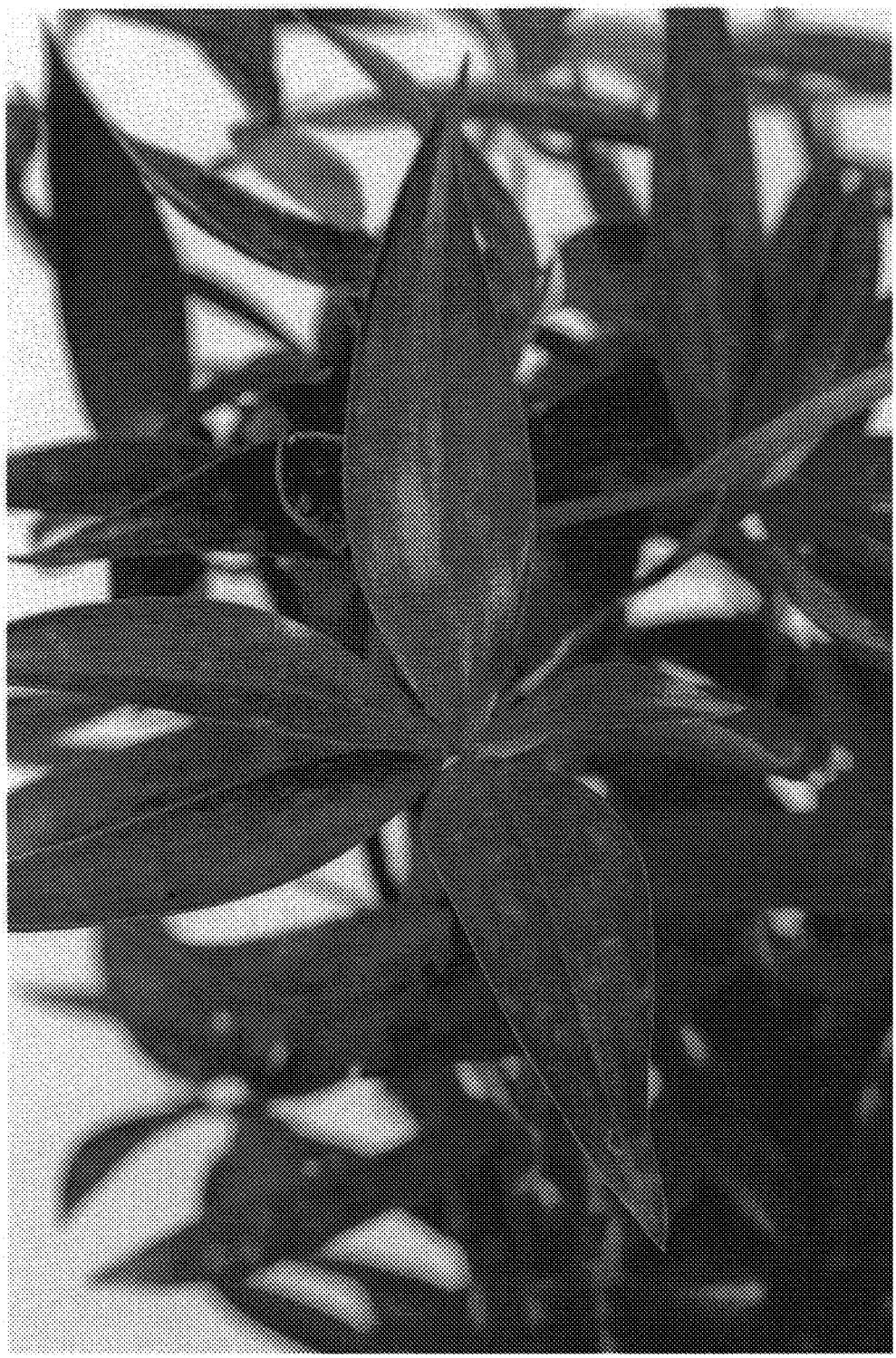
FIG. 2 illustrates, as nearly true as it is reasonably possible to make the same in color photographs of this type, the typical juvenile and intermediate foliage of 'CANTIK'.

The following observations and measurements, made in September of 2018, describe averages from a sample set of six specimens of two year-old 'CANTIK' plants grown in 23 cm nursery pots in Kota Tinggi, Johor, Malaysia. Plants were produced using conventional greenhouse production protocols for *Dracaena* sp. which consisted of growing under shade cloth, irrigating at regular intervals with ebb and flow flood benches, and fertigation. No chemical treatments of any kind were utilized.

Those skilled in the art will appreciate that certain characteristics will vary with older or, conversely, with younger plants. 'CANTIK' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'CANTIK' and comparisons with the parent plant and most similar commercial *Dracaena* cultivar known to the inventor are provided below.

Plant description:

*Growth habit*.—Perennial; upright.

*Plant profile*.—Obovate to broad elliptical.

*Average height from base to top of foliage*.—71.5 cm.

*Average width*.—Average of 57.0 cm.

*Growth rate*.—Moderately fast growing.

*Plant vigor*.—Moderately vigorous to vigorous.

*Propagation details*.—Asexual propagation is accomplished by softwood stem cuttings.

*Time to initiate roots*.—Approximately 16 weeks are required to initiate roots at 20 degrees Celsius.

*Disease and pest resistance or susceptibility*.—Neither tolerance nor resistance to normal diseases and pests of *Dracaena japonicus* have been observed.

*Environmental tolerances*.—Adapt to USDA Hardiness Zones 10 through 12 and temperatures as high as 40 degrees Celsius; moderate tolerance to rain and wind.

Root system:

*General*.—Fibrous; freely branched and moderately dense rooting.

*Distribution in the soil profile*.—Shallow to moderately deep.

*Texture*.—Smooth; glabrous.

*Color*.—Greyed-orange, RHS N170A.

Stems:

*Branching habit*.—Main stems grow from the plant's base, freely branching with lateral branches.

*Number of main stems per plant*.—55.

*Number of lateral branches per plant*.—50.

*Aspect*.—Rounded.

*Length of main stems*.—49.0 cm.

*Diameter of main stems*.—Averaging 0.4 cm at the widest point.

*Internode length on main stems*.—0.5 cm.

*Attitude*.—Main stems are near vertical; lateral branches at an average angle of 50 degrees to the main stems.

*Strength*.—Very strong.

*Texture*.—Smooth; glabrous.

*Luster*.—Moderately glossy.

*Color, juvenile*.—Yellow-green, RHS 144A.

*Color, mature*.—Yellow-green, RHS 148A.

*Color at internodes*.—Greyed-orange, RHS 165C.

Foliage:

*Arrangement*.—Opposite; foliage is clustered at and near the apex of the lateral branches.

*Attachment*.—Petiolate.

*Division*.—Simple.

*Attitude*.—Foliage is at an approximate angle of 50 degrees to the lateral branches.

*Number of leaves per lateral branch*.—6.

*Lamina*.—Dimensions — 9.2 cm long and 2.5 cm wide, on average. Shape — Lanceolate. Aspect — Slightly curved; distal portion on the lamina pointing horizontally. Apex — Narrowly acute. Base — Attenuate. Margin — Finely crenate to serrulate. Texture and luster of adaxial surface — Smooth, glabrous and glossy. Texture and luster of abaxial surface — Smooth, glabrous and moderately glossy. Color — Juvenile foliage, adaxial surface — In between green and yellow-green, RHS 143A and 144A; sparsely and irregularly dotted yellow-green, RHS 144B. Juvenile foliage, abaxial surface — In between green and yellow-green, RHS 143C and 144A; sparsely and irregularly dotted yellow-green, RHS 144B. Mature foliage, adaxial surface — In between green and yellow-green, RHS 143A and 147A; sparsely to moderately and irregularly dotted yellow-green, RHS 144B. The average diameter of the dots is 0.25 cm. Mature foliage, abaxial surface — In between green and yellow-green, RHS 143A and 146B; sparsely to moderately and irregularly dotted yellow-green, RHS 144B. The average diameter of the dots is 0.25 cm. Aging foliage, adaxial surface — In between green and yellow-green, RHS NN137A and 147A; irregularly blushed and marbled green, RHS 143A. The average diameter of the dots is 0.8 cm. Aging foliage, abaxial surface — Green, RHS 137B; irregularly blushed green, RHS 143B. The average diameter of the blushes is 0.8 cm. Venation — Pattern — Pinnate. Color, adaxial surface — The midrib is in between green and yellow-green, RHS 143A and 144A. All other veins are indistinguishable from the surrounding foliage. Color, abaxial surface — Yellow-green, RHS 144A. All other veins are indistinguishable from the surrounding foliage.

Petiole:

*Length*.—0.45 cm.

*Width*.—0.3 cm.

*Texture*.—Glabrous; smooth.

*Luster*.—Matte on the adaxial surface; moderately glossy on the abaxial surface.

*Strength*.—Moderately strong.

*Color, adaxial surface*.—Green, RHS 143A.

*Color, abaxial surface*.—Green, RHS 143C.

Bracts:

*Quantity*.—1.

*Position*.—At the node.

*Shape*.—Narrowly triangular.

*Dimensions*.—2.2 cm long and 0.5 cm wide.

*Apex*.—Narrowly acuminate.

*Base*.—Broad cuneate.

*Color, adaxial and abaxial surfaces*.—Nearest to in between greyed-yellow and greyed-orange, RHS 161B and 165D.

*Base*.—Broad cuneate.

Inflorescence: To date, flowering has not been observed.

Flower buds: To date, flowering has not been observed.

Flower: To date, flowering has not been observed.

Reproductive organs: To date, flowering has not been observed.

Seed and fruit: To date, flowering has not been observed.

COMPARISONS WITH THE PARENT PLANT AND CLOSEST KNOWN COMMERCIAL VARIETY

Plants of the new cultivar 'CANTIK' may be distinguished from its parent, an unnamed *Dracaena surculosa* plant (not patented), by the characteristics described in Table 1.

TABLE 1

| Characteristic | 'CANTIK' | The parent. |
|---|---|---|
| Foliage shape. | Lanceolate but broader than the parent. | Lanceolate but narrower than 'CANTIK'. |
| Foliage size. | Smaller than the parent. | Larger than 'CANTIK'. |
| General coloration of the foliage. | Darker green when compared to the parent. | Lighter green when compared to 'CANTIK'. |

Plants of the new cultivar 'CANTIK' may be distinguished from the closest known commercial comparator, *Dracaena surculosa* 'DRACMIK04' (Community Plant Variety Rights application number 2016/3037), by the characteristics described in Table 2.

TABLE 2

| Characteristic | 'CANTIK' | 'DRACMIK04' |
|---|---|---|
| Plant height. | Taller than 'DRACMIK04'. | Shorter than 'CANTIK'. |
| General coloration of the foliage. | Darker green when compared to 'DRACMIK04'. | Lighter green when compared to 'CANTIK'. |
| Presence of axial striations. | No axial striations. | Irregular axial striations are present at and near the central zone of the foliage. |
| Prominence of colored dots on the foliage. | Inconspicuous light green dots. | Prominent yellow dots. |

That which is claimed is:

1. A new and distinct cultivar of *Dracaena* plant named 'CANTIK', substantially as described and illustrated herein.

* * * * *